United States Patent [19]

Heine et al.

[11] Patent Number: 4,756,192
[45] Date of Patent: Jul. 12, 1988

[54] SHOCK WAVE SENSOR

[75] Inventors: Gerold Heine, Uhldingen-Muehlhofen; Joachim Stark, Friedrichshafen, both of Fed. Rep. of Germany

[73] Assignee: Dornier System GmbH, Friedrichshafen, Fed. Rep. of Germany

[21] Appl. No.: 785,879

[22] Filed: Oct. 9, 1985

[30] Foreign Application Priority Data

Oct. 17, 1984 [DE] Fed. Rep. of Germany ....... 3437976

[51] Int. Cl.[4] ............................................. G01N 29/00
[52] U.S. Cl. ...................................... 73/632; 310/334; 367/165
[58] Field of Search ................... 73/649, 632; 310/800, 310/321, 327, 322, 334, 335, 336; 367/165, 163, 141

[56] References Cited

U.S. PATENT DOCUMENTS

| 2,587,304 | 2/1952 | Fiske, Jr. et al. | 367/165 |
| 3,255,431 | 6/1966 | Howatt | 367/165 |
| 4,433,400 | 2/1984 | DeReggi et al. | 310/800 |
| 4,544,859 | 10/1985 | Eoff | 310/800 |

OTHER PUBLICATIONS

P. A. Lewin, "Miniature Piezoelectric Polymer Ultrasonic Hydrophone Probes", *Ultrasonics,* pp. 213–215, Sep. 1981.

*Primary Examiner*—Michael J. Tokar
*Assistant Examiner*—Hezron E. Williams
*Attorney, Agent, or Firm*—Ralf H. Siegemund

[57] ABSTRACT

A shock wave sensor is disclosed in which a piezoelectric foil is either suspended in a ring or on a backing. Electrodes run from a particular sensitive area on the foil towards the edges and are fracture proof connected to concentric conductors.

1 Claim, 2 Drawing Sheets

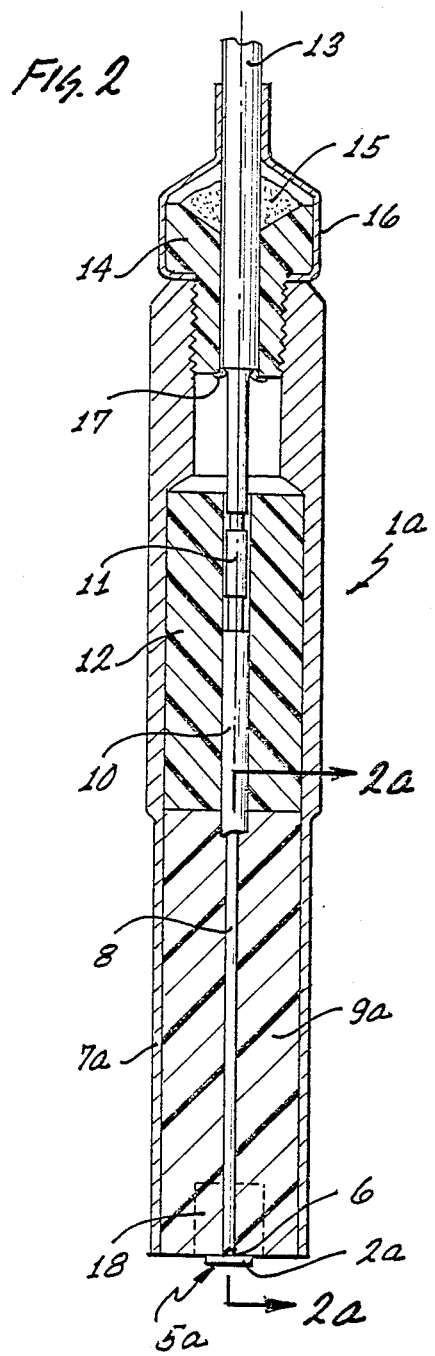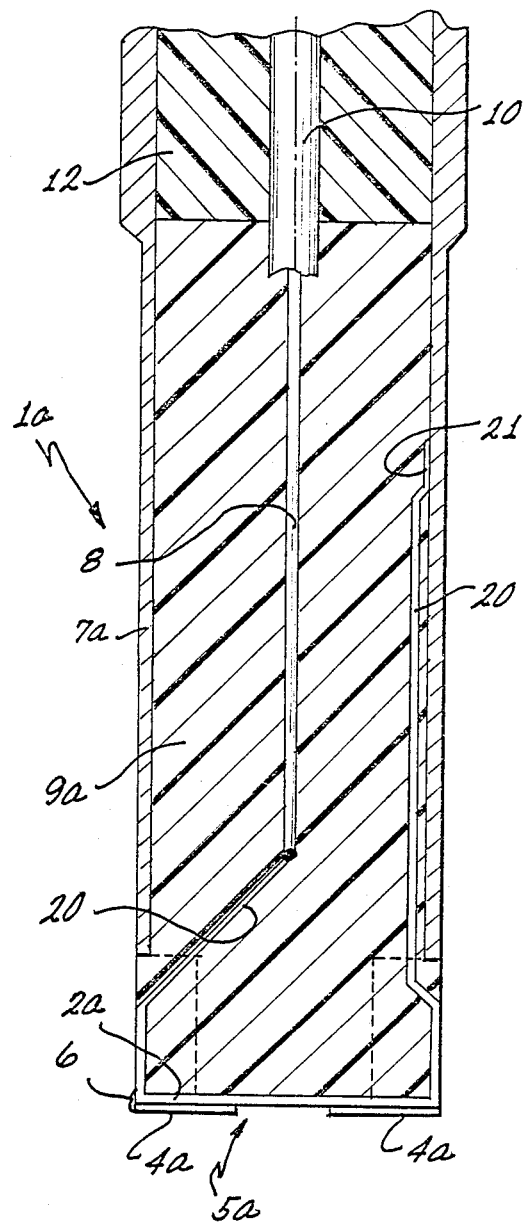

SHOCK WAVE SENSOR

BACKGROUND OF THE INVENTION

The present invention relates to a shock wave sensor and, more particularly, the invention relates to a shock wave sensor wherein a hollow, carryng shaft is concentrically arranged around another electrode structure, both being connected to piezo electric foil means.

Shock wave sensors are used, for example, for measuring the pressure amplitude of a shock wave as it propagates in a medium, for example, water. A particularly important field of application is the measurement of the pressure in the focal point of shock waves which have been focused.

Qualitatively, shock waves are similar to ultrasonic waves, but these two types of waves differ quantitatively in that shock waves have a very steep leading edge-like onset, a very high pressure peak, and a more or less rapid decay thereafter. Also, shock waves do not have any basic periodicity. This, of course, is due to the fact that the frequency spectrum of shock waves is considerably wider than in the case of ultrasonic waves.

So-called hydrophones are used for detecting ultrasonic waves. They include foils made of a piezo electric polymer, preferably polyvinylidenfluoride ($PVF_2$ or PVDF). K. C. Shotton, et al. described a hydrophone in "Ultrasonics," 1980, page 123. This hydrophone has a very high sensitivity for the detection of ultrasonic waves. However, it is believed that this kind of hydrophone is unsuitable for the detection of shock waves because the vapor deposited contact devices will be removed by an erosive process caused primarily by cavitation. In fact, these vapor deposited layers will decay very rapidly.

P. A. Lewin describes a hydrophone in "Ultrasonics," September 1981, page 213, but it is analogously defective because shock waves would crack the contact areas of the sensor elements being directly mounted to a rigidly constructed housing. It thus can be seen that ultrasonic hydrophones as per the state of the art are not sufficiently robust for use in the detection of shock waves or shock wave fields.

A shock wave sensor designed specifically for that purpose and for measurements within that field is, for example, described by S. W. Meeks, et al. in the "Journal of the Acoustical Society of America," 1984, page 1010. Therein a thick $PVF_2$ foil, being about 500 micrometers thick, is used and suspended together with several disks within a three-legged frame. The thickness of the foil, however, reduces the band width of the sensor considerably and renders it sensitive to the detection of transverse waves.

DESCRIPTION OF THE INVENTION

It is an object of the present invention to provide a new and improved shock wave sensor which overcomes the difficulties outlined above, particularly concerning mechanical stability or lack thereof in prior art hydrophone devices. On the other hand, the shock wave sensor is to have a sufficiently high sensitivity covering a large band width and should be capable of registering even very rapid signal onsets in the range of 10 nanoseconds, without distorsions and without developing parasitic natural oscillations. Moreover, the construction should be such that is is capable of withstanding very high pressures without loss in use life.

In accordance with the preferred embodiment of the present invention, it is suggested to improve a coaxial arrangement of an inner conductor and of a rigid hollow outer conductor by providing a piezo electric foil which is relatively thin and is connected in a fractureproof fashion and by means of electrodes deposited on the foil, to the two conductors. The foil is provided on a much thicker carrier being made of a similar material or other sound attenuating material, and thin wires are used for contact making. Contact making is provided well outside of the sensing area. The contact making may generally include an electrically conductive adhesive or soldering. In some cases it may be advisable to provide the tubular outer conductor with slots or recesses in order to ensure that the foil is kept away from that rigid part of the arrangement. The foil may, as an additional precaution, be provided with an insulating layer. The sensor in accordance with the invention has indeed a high band width, i.e., a band width in excess of 20 Mhz.; it does not develop pronounced natural resonance frequencies higher than 100 Khz. and will be capable of maintaining its function for more than 10,000 shock waves of an amplitude peak of about 1/10 GPa. It is believed to be essential for the invention that the foil should be quite thin, i.e., larger than about 5 micrometers but not exceeding 50 micrometers, which dimension can be interpreted as a definition for the term "thin." Moreover, the particular way of contact making is highly beneficial. Contact making is carried out either outside of the shock wave ranges (spatially), i.e. of an area that is to be used for detecting the focal point of focused shock waves. A small foil is used for other purposes with contact areas being suspended in a particular soft fashion. Most importantly, the electrodes do not engage or are in contact with the rigid housing or casing. In the latter case, the foil is bonded onto an attenuating carrier or backing made of the same material or of a particular attenuating material and is thus attenuated with regard to vibrations vis-a-vis the metallic hollow carrying tube. The voltage extraction from the electrodes is carried out through utilization of thin wires which are run through the attenuating backing towards the shaft hollow outer tube and they are also run to the inner conductor. Most importantly, the electrodes on the foil do not engage the rigid hollow metal tube anywhere. The solder or other bonding areas will therefore experience only a highly reduced mechanical load whenever a shock wave passes.

The contact making in accordance with the invention, including voltage extraction and contact making generally, is carried out through thin foils having the advantage of a very high resonance frequency for thickness vibrations and a very high strength vis-a-vis bending and shear loads. Moreover, the inventive sensors exhibit a very low impedance difference as compared with the working medium in which they are inserted.

In order to avoid damages as a result of cavitation processes, the sensor foil may be protected in addition by means of a thin isolating layer such as aluminum oxide or silicon oxide, preferably having a thickness of about 10 micrometers. In case of a foil on a backing, however, the protection through such a layer is needed only on the front.

may be protected on one or even both sides by means of such a layer. In case of a foil on a backing, however, the protection through such a layer is needed only on the front.

DESCRIPTION OF THE DRAWINGS

The specification concludes with claims particularly pointing out and distinctly claiming the subject matter which is regarded as the invention. It is believed that the invention, the objects and features of the invention, and further objects, features and advantages thereof will be better understood from the following description taken in conjunction with the accompanying drawings in which:

FIG 2 is a right angle section view through a portion of FIG. 1.

Proceeding, now, to the detailed description of the drawings, FIGS. 1 and 2 illustrate an example of the inventive sensor identified here by reference numeral 1a. There is a piezo electric PVDF foil 2a which in this case is of rectangular configuration. The length of this foil corresponds to the diameter of a cylindrical conductor and tubular holding device 7a. The width of this foil 2a is smaller than the width of a slot 18 within the tube 7a (see FIG. 1, bottom). The foil 2a is bonded onto a carrier or backing 9a which is either made of PVDF material or of a sound attenuating material. It is decisive that the foil 2a does not engage the tube 7a anywhere. The tube 7a, just as in the other example, is of rigid construction.

Figure 1:
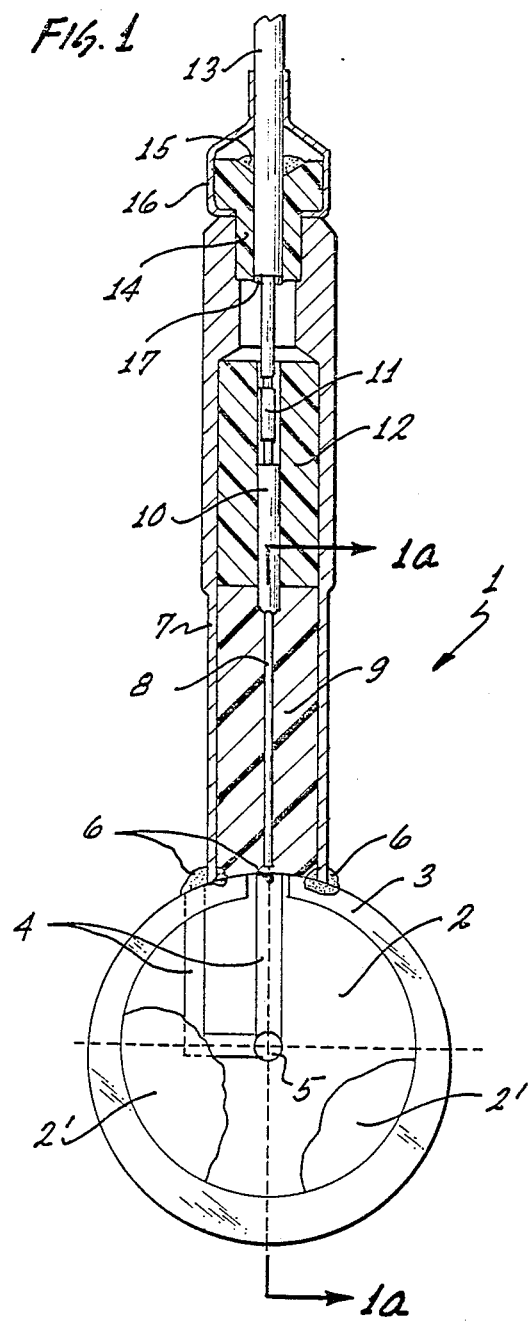
FIG. 1 is a longitudinal section view of a shock wave sensor constituting an example for the preferred embodiment of the present invention, for practicing the best mode thereof in an environment in which local but unfocussed shock waves are to be detected.
Figure 1A:
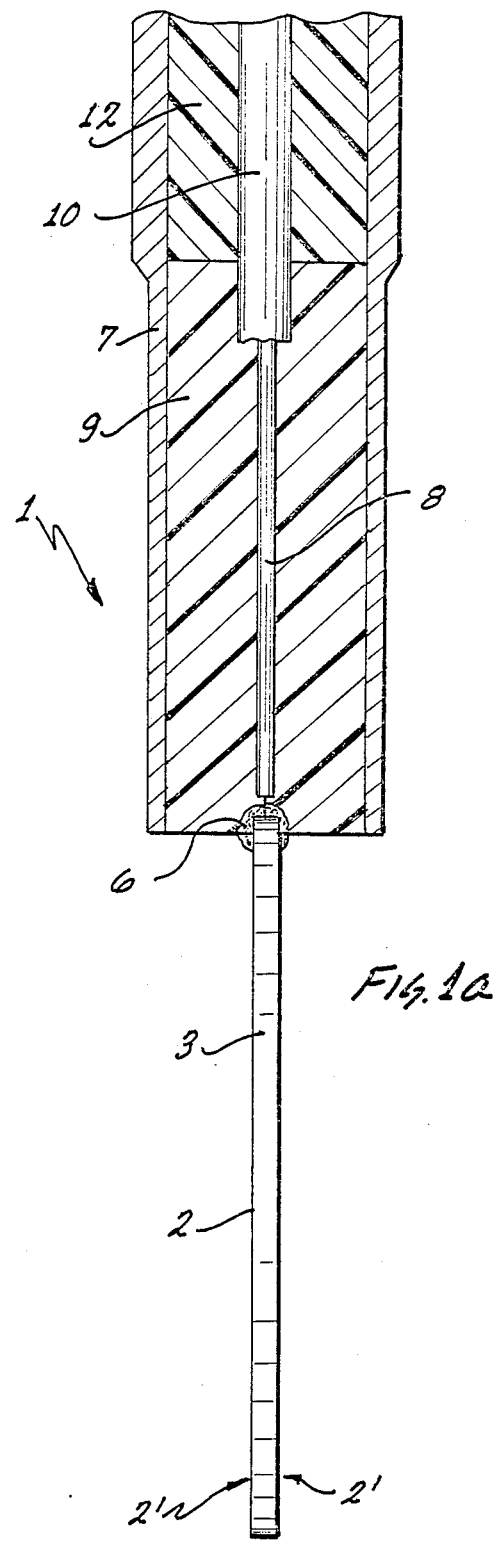

The electrodes 4a run from the principally sensitive sensor area 5a of the foil 2a toward the edges thereof. The electrodes 4a are grossly exaggerated as to thickness in FIG. 2a. Here, now, the electrodes 4a are secured to the inner conductor 8 as well as the metallic tube 7a by means of an adhesive 6 defining the area of contact, and thin wires 20 are used for the connection to the conductors 7a, 8a. Reference numeral 21 refers to another soldering.

In the following, examples are given concerning preferred dimensions for several components. They refer specifically to the thickness of relevant layers in the sensing area 5a being traversed by incident shock waves. The electrode layer 4a should be about 300 Angstroms thick. The PVDF foil 2a should be between 9 and 40 micrometers thick. As the case may be, any second electrode 4a should likewise be 300 Angstroms thick. The bonding layer between backing and foil 2a in the example of FIG. 1 should be between 6 and 20 micrometers thick. A protective layer on top of the foil and provided against cavitation has a thickness of not more than 10 micrometers. The carrier or backing 9a in FIG. 1 should be several millimeters thick.

The invention is not limited to the embodiments described above, but all changes and modifcations thereof not constituting departures from the spirit and scope of the invention are intended to be included in the claims.

We claim:

1. A shock wave sensor having an inner conductor and an outer tubular conductor serving as housing and being arranged coaxially to the inner conductor, the improvement comprising:

a piezo electric rectangular foil;

a relatively thick carrier in said tubular conductor being made of PVDF or a sound attenuating material for suspending said foil on said tubular conductor, said foil being provided with electrode layers on the side facing away from the carrier;

there being indents or recesses in the outer tubular conductor near the foil to ensure spatial separation of the foil from the tubular conductor; and contact making means including relatively thin wires for fracture-proof connecting said electrode layers respectively with said tube and said inner conductor, and on said side of said foil being of a sensing area of said foil.

* * * * *